US012559721B2

(12) United States Patent
Soh

(10) Patent No.: US 12,559,721 B2
(45) Date of Patent: Feb. 24, 2026

(54) METHOD FOR ISOLATING A CARDIOMYOCYTE POPULATION

(71) Applicant: Agency for Science, Technology and Research, Singapore (SG)

(72) Inventor: Boon Seng Soh, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 1046 days.

(21) Appl. No.: 17/260,049

(22) PCT Filed: Jul. 16, 2019

(86) PCT No.: PCT/SG2019/050346
§ 371 (c)(1),
(2) Date: Jan. 13, 2021

(87) PCT Pub. No.: WO2020/018019
PCT Pub. Date: Jan. 23, 2020

(65) Prior Publication Data
US 2021/0317412 A1    Oct. 14, 2021

(30) Foreign Application Priority Data
Jul. 16, 2018    (SG) ............................ 10201806072Q

(51) Int. Cl.
C12N 5/077       (2010.01)
A61K 35/34       (2015.01)
G01N 33/569      (2006.01)

(52) U.S. Cl.
CPC ............ *C12N 5/0657* (2013.01); *A61K 35/34* (2013.01); *G01N 33/56966* (2013.01)

(58) Field of Classification Search
CPC .............................. C12N 5/0657; A61K 35/34
See application file for complete search history.

(56) References Cited

U.S. PATENT DOCUMENTS 9,717,762 B2    8/2017  Weincierz

FOREIGN PATENT DOCUMENTS

| WO | WO 2016/131137 | 8/2016 | |
| WO | WO 2016/201129 | 12/2016 | |
| WO | WO 2017/207576 | 12/2017 | |
| WO | WO-2017207576 A1 * | 12/2017 | ............ A61K 35/34 |
| WO | WO 2018/224983 | 12/2018 | |

OTHER PUBLICATIONS

Lee, Yee-Ki, et al. "Calcium homeostasis in human induced pluripotent stem cell-derived cardiomyocytes." Stem Cell Reviews and Reports 7 (2011): 976-986. (Year: 2011).*

Wiencierz, Anne Maria, et al. "Differential expression levels of integrin a6 enable the selective identification and isolation of atrial and ventricular cardiomyocytes." PLoS One 10.11 (2015): e0143538. (Year: 2015).*

Dubois, Nicole C., et al. "SIRPA is a specific cell-surface marker for isolating cardiomyocytes derived from human pluripotent stem cells." Nature biotechnology 29.11 (2011): 1011-1018. (Year: 2011).*

Fan, Gaowei, et al. "Bispecific antibodies and their applications." Journal of hematology & oncology 8 (2015): 1-14. (Year: 2015).*

Brinkmann, Ulrich, and Roland E. Kontermann. "The making of bispecific antibodies." MAbs. vol. 9. No. 2. Taylor & Francis, 2017. (Year: 2017).*

International Preliminary Report on Patentability for International Application No. PCT/SG2019/050346, "Method for Isolating a Cardiomyocyte Population", Date of Mailing: Jan. 19, 2021.

Ban K. et al., Current Strategies and Challenges for Purification of Cardiomyocytes Derived from Human Pluripotent Stem Cells. *Theranostics*, May 17, 2017, vol. 7, No. 7, pp. 2067-2077.

Burridge, P. W., Keller, G., Gold, J. D. & Wu, J. C. "Production of de novo cardiomyocytes: human pluripotent stem cell differentiation and direct reprogramming" *Cell stem cell* 10, 16-28 (Jan. 6, 2012).

Cambria, E., et al, "Translational cardiac stem cell therapy: advancing from first-generation to next-generation cell types", npj Regenerative Medicine (2017)2:17, 10 pages.

Cheung K.-K. et al., Pharmacological and molecular characterization of functional P2 receptors in rat embryonic cardiomyocytes. *Purinergic Signalling*, Dec. 16, 2014, vol. 11, No. 1, pp. 127-138.

Dubois N.C. et al., SIRPA is a specific cell-surface marker for isolating cardiomyocytes derived from human pluripotent stem cells. *Nat Biotechnol*, Oct. 23, 2011, vol. 29, No. 11, pp. 1011-1018.

Hotkar, A.J., et al., "Stem Cells in the Treatment of Cardiovascular Disease—An Overview", *Stem Cell Rev and Rep* 8, 494-502 (2012). https://doi.org/10.1007/s12015-011-9302-2.

(Continued)

*Primary Examiner* — Maria G Leavitt
*Assistant Examiner* — Michael Angelo Riga
(74) *Attorney, Agent, or Firm* — Hamilton, Brook, Smith & Reynolds, P.C.

(57) ABSTRACT

The present application relates to, inter alia, the identification, isolation and/or purification of cardiomyocytes in a sample. The method for isolating a cardiomyocyte population from a heterogeneous population of differentiated cells comprises: (a) contacting the sample with at least one agent that specifically binds to at least one cardiomyocyte surface marker selected from JAK2, DDR2, ACVRL1, CD200, SRPX, PRKACB, MST1R, P2RX1, TNFRSF10A, CHRND, KIAA0319, CD274, CCRL2, MBL2, ADORA3 and CD181; and (b) isolating the cells bound to the said agent. A preferred embodiment comprises contacting the sample with a first agent that specifically binds to a cell surface marker selected from JAK2, DDR2, ACVRL1, CD200, SRPX, PRKACB and MST1R to provide ventricular cardiomyocytes and a second agent that specifically binds to a cell surface marker selected from P2RX1, TNFRSF10A, CHRND, KIAA0319, CD274, CCRL2, MBL2, ADORA3 and CD181 to provide atrial cardiomyocytes. Another embodiment relates to the use of the isolated cardiomyocyte population for treating cardiovascular disease or disorder.

10 Claims, 4 Drawing Sheets

(56) References Cited

OTHER PUBLICATIONS

Figure 1:
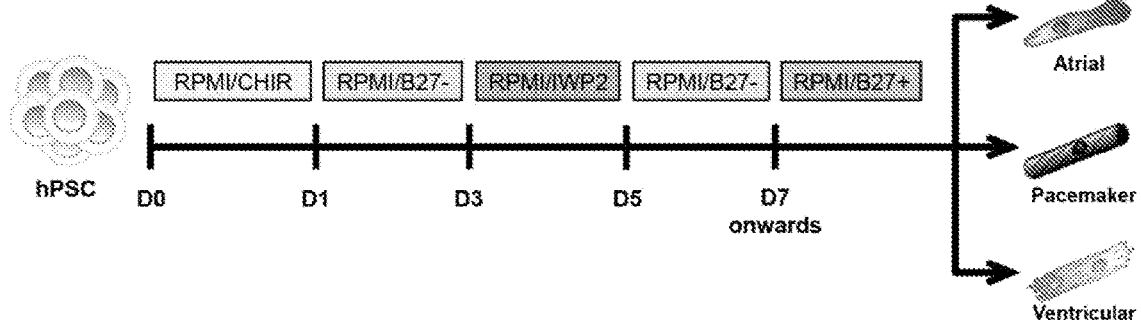
Figure 1:
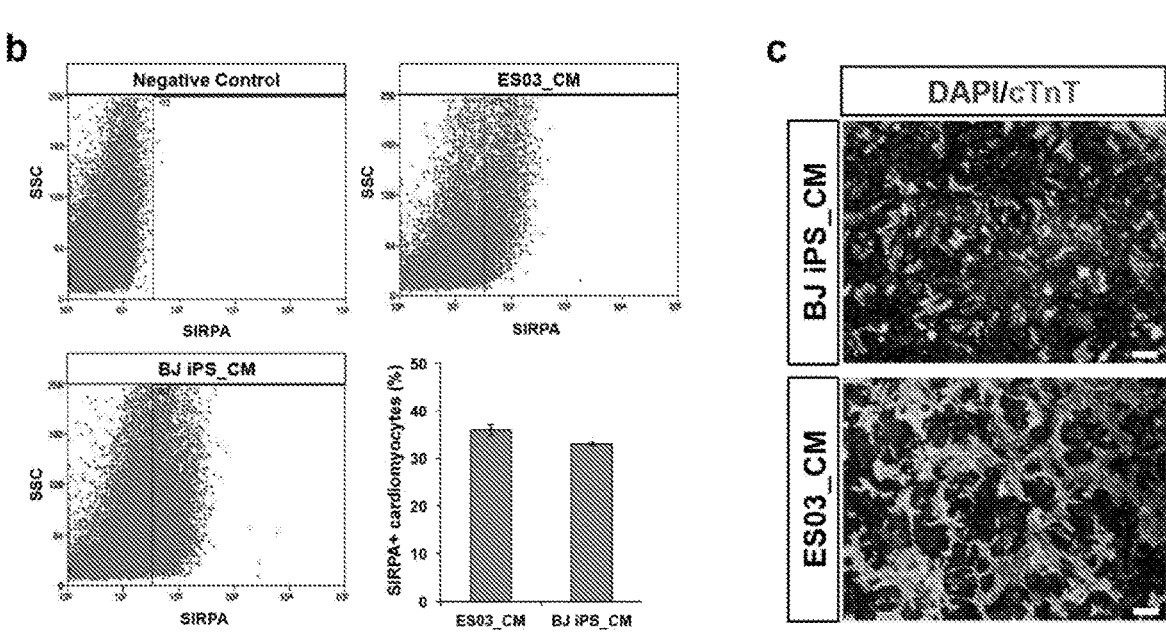

Hrvatin, S., Deng, F., O'Donnell, C. W., Gifford, D. K. & Melton, D. A. Maris: method for analyzing RNA following intracellular sorting. *PloS one* 9, e89459 (Mar. 2014).

Huber I. et al., Identification and selection of cardiomyocytes during human embryonic stem cell differentiation. *FASEB Journal*, Apr. 13, 2007, vol. 21, No. 10, pp. 2551-2563.

International Search Report for International Application No. PCT/SG2019/050346, "Method for Isolating a Cardiomyocyte Population", Date of Mailing: Oct. 9, 2019.

Laflamme, M. A. & Murry, C. E. Regenerating the heart. *Nature biotechnology* 23, 845-856 (Jul. 2005).

Lian, X. et al. "Directed cardiomyocyte differentiation from human pluripotent stem cells by modulating Wnt/β-catenin signaling under fully defined conditions", *Nature protocols* 8, 162-175 (Jan. 2013).

Lian, X. et al. Robust cardiomyocyte differentiation from human pluripotent stem cells via temporal modulation of canonical Wnt signaling. *Proceedings of the National Academy of Sciences of the United States of America* 109, E1848-1857 (May 29, 2012).

Poon E. et al., Transcriptome-Guided Functional Analyses Reveal Novel Biological Properties and Regulatory Hierarchy of Human Embryonic Stem Cell-Derived Ventricular Cardiomyocytes Crucial for Maturation. *PLOS ONE*, Oct. 21, 2013, vol. 8, No. 10, pp. e77784.

Wiencierz A.M. et al., Differential Expression Levels of Integrin a6 Enable 1, 2 AND 4-23 the Selective Identification and Isolation of Atrial and Ventricular Cardiomyocytes. *PLOS ONE*, Nov. 30, 2015, vol. 10, No. 11.

Written Opinion for International Application No. PCT/SG2019/050346, "Method for Isolating a Cardiomyocyte Population", Date of Completion: Mar. 10, 2019.

* cited by examiner a b c

METHOD FOR ISOLATING A CARDIOMYOCYTE POPULATION

This application is the U.S. National Stage of International Application No. PCT/SG2019/050346 filed Jul. 16, 2019, which designates the U.S., published in English, and claims priority under 35 U.S.C. § 119 or 365(c) to SG application Ser. No. 10201806072Q, filed Jul. 16, 2018. The entire teachings of the above applications are incorporated herein by reference.

The present invention relates to the purification of cardiomyocytes in a sample.

Cardiovascular disease (CVD) remains the leading cause of death worldwide. Damage to the heart resulting from cardiovascular disease leads to gradual loss of function and reduced quality of life. Cardiac injury is particularly debilitating, more so than injury to any other organ, given our current inability to either generate new and functional cardiac tissue or to mimic the actions of the heart using external devices. Cardiovascular disease arising from multi-facet of events can lead to detrimental consequences, which include the formation of fibrotic scar tissue and reduced distension capacity of blood vessels leading to the heart. The resulting overload of blood flow and pressure leads to irreversible damage to cardiomyocytes, heart failure and eventually death.

Over several decades, the use of drug-based or device-based therapies to treat CVD (e.g arrhythmias) has been fraught with difficulties of ineffectiveness or inadequacies associated with side effects. This motivated the recent advancements and research in stem cell-based therapies. For instance, generating human pluripotent stem cells (hPSCs) derived cardiomyocytes aimed at creating a platform for identifying genetic variants underlying cardiovascular diseases that accurately recapitulates the disease phenotype in vitro. More recently, advancement in stem cell therapy for cardiovascular disease has highlighted the potential for the use of stem cell therapy in providing unlimited supply of functional cardiomyocytes to restore cardiac function, through repair or regeneration of the damaged heart tissue (Hotkar and Balinsky, 2012). Whilst earlier studies have reported the benefits of cell-based therapy which resulted in improved cardiac function in animal models (Cambria et al., 2017), we question whether the risk of complications associated with tissue rejection or arrhythmias may still occur upon tissue implantation, as current available cell surface markers are often non-specific for the purification of specific cardiomyocyte sub-populations (atrial, ventricular or pacemaker).

Whilst stem cell therapy offers new revenue for cell-based therapies to replace heart tissues damaged by disease or age[1,2], the use of mixed population of cells in vitro can be problematic, as the contaminating populations may influence the disease outcomes, as well as alter the effect of cardiovascular grafts used in translational medicine.

It had previously been reported that SIRPA may be used as a specific cell-surface marker for the isolation of cardiomyocytes derived from human pluripotent stem cell (Dubois et al. Nat. Biotechnol. 2011). However, SIRPA alone was unable to distinguish between specific cardiomyocyte populations such as ventricular and atrial cardiomyocytes. The purification of specific cardiomyocyte sub-populations is important, in particular for cell-based therapy since cardiomyocyte sub-populations exhibit different electrophysiological properties.

As such, the present invention attempts to identify cell surface markers that are specific to cardiomyocyte sub-populations, and subsequently demonstrated that atrial or ventricular cardiomyocytes can be isolated and purified using these specific extracellular markers. This invention therefore enables purification of specific cardiomyocyte sub-populations, which can be used for cell-based therapy targeting specific regions of the patients hearts and leading to reduced complications arising from arrhythmia.

The listing or discussion of an apparently prior-published document in this specification should not necessarily be taken as an acknowledgement that the document is part of the state of the art or is common general knowledge.

Any document referred to herein is hereby incorporated by reference in its entirety.

The present invention relates to specific cell surface markers for the isolation of either atrial or ventricular cardiomyocytes.

Hence, in a first aspect of the present invention, there is provided a method for isolating a cardiomyocyte population from a heterogeneous population of differentiated cells in a sample, the method comprising: (a) contacting the sample with at least one agent that specifically binds to at least one cardiomyocyte surface marker; and (b) isolating the cells bound to the said agent, wherein the cardiomyocyte surface marker is selected from Table 1 shown below.

TABLE 1

| Cardiomyocyte cell surface markers | |
|---|---|
| A | JAK2, DDR2, ACVRL1, CD200, SRPX, PRKACB, MST1R |
| B | P2RX1, TNFRSF10A, CHRND, KIAA0319, CD274, CCRL2, MBL2, ADORA3, CD181 |

By "isolating", it is mean to refer to a cell, isolatable or purified from other components. An isolated cell refers to a cell free from the environment in which it may naturally occur. The isolated cell may be purified to any degree relative to its naturally-obtainable state. In addition, the term is also meant to include identifying, enriching, differentiating and distinguishing (for example, in the present context, distinguishing between cardiomyocyte sub-types).

To date, there have been no published methods for enriching for cardiomyocytes based on the cell surface markers of the present invention. The present invention provides significantly greater levels of enrichment of cardiomyocytes compared with prior art methods available to date. Furthermore, existing methods for selecting for cardiomyocytes have relied upon the use of mitochondrial staining in combination with flow cytometry or magnetic cell separation methods. Older methodologies require centrifugation across percoll gradients, which are technically challenging and time consuming. The present invention thus permits the facile enrichment of cardiomyocytes based on recognition of cell surface markers. The inventors have found that cell populations enriched for cardiomyocytes can be selected based on expression of the cell surface markers CD200, JAK2, CD181 and CHRND, or the combination of any one of these cell surface markers.

The stem cell sample may be a heterogeneous population of differentiated stem cells. Methods for culturing a sample according to the present disclosure will be known to persons skilled in the art and are described elsewhere in this document. In various embodiments, the sample comprises cardiomyocytes differentiated in culture from a stem cell or progenitor cell. In one example, the stem cell is a pluripotent stem cell. In another example, the pluripotent stem cell is a human embryonic stem cell (hES cell). Methods for causing differentiation of stem (including pluripotent stem) or progenitor cells are known in the art and are explained in further detail elsewhere in this document. In one example, the differentiation of the cells is biased towards cells of the cardiac lineage. Methods for biasing differentiation of cells towards the cardiac lineage will be known to persons skilled in the art. The cells may be in the process of becoming fully differentiated or may be fully differentiated. Suitable pluripotent cells according to the present disclosure include human embryonic stem cells (hES), embryonic stem cells from other primates, such as Rhesus stem cells or marmoset stem cells and human embryonic germ (hEG) cells, induced pluripotent stem cells (iPS), or stem cells lines such as but not limited to BG01, BG02, HUES cell lines e.g. HUES1-17, HES2 or HES3 or human ESC-derived cardiac progenitor cells (e.g. hESC-CPCs).

In another example, the sample comprises a mixed population of cells comprising cardiomyocytes. In another example, the mixed population of cells comprises any cell type that is capable of differentiating down the cardiac lineage. In a further example, the mixed population of cells includes pluripotent cells, cardiac progenitor cells, induced pluripotent stem cells (iPS), induced/re-programmed cardiomyocyte cells, umbilical tissue, left atrial appendage, cardiac tissue, circulating endothelial cells, cardiac fibroblasts, adipose tissue or skin tissue and combinations thereof.

In one example, the mixed population of cells comprises differentiating pluripotent cells and/or the progeny thereof.

In another example, the sample or the mixed population of cells according to the present disclosure are human derived. In one example, the cells are human derived pluripotent cells. However, it is also envisaged that primate pluripotent cells may be suitable for use according to any method disclosed therein. The sample or the mixed population of cells according to the present disclosure may be autologous, or allogeneic.

In one particular example, the pluripotent cells are human embryonic stem (hES) cells. The preferred progeny may include committed cardiac progenitor cells (CPCs) or cells derived from committed cardiac progenitor cells. In one example, the progeny cells are cardiomyocytes. In one example, the cardiomyocytes are human cardiomyocytes. In a preferred example, the method of the present disclosure enriches for human cardiomyocytes.

By "stem cells", it is meant to refer to a stem cell that is undifferentiated prior to culturing and is capable of undergoing differentiation. The stem cells may be selected from a group consisting of embryonic stem (ES) cell, pluripotent stem cells, hematopoietic stem cells, totipotent stem cells, mesenchymal stem cells, neural stem cells and adult stem cells. In particular the stem cell may be human embryonic stem (hES) cells. For example the stem cell may be derived from a cell culture, such as hES cells. The stem call may be derived from an embryonic cell line or embryonic tissue. The embryonic stem cells may be cells which have been cultured and maintained in an undifferentiated state.

By "differentiated cell", it is meant to refer to a cell that has progressed further down the developmental pathway than a cell with which it is being compared. Thus, embryonic stem cells can differentiate to lineage restricted progenitor cells (such as a mesodermal stem cell), which in turn can differentiate into other types of progenitor cells further down the pathway (such as cardiomyocyte progenitors), and then to an end-stage differentiated cells, which plays a characteristic role in a certain tissue type, and may or may not retain the capability to proliferate further.

The potential of ES cells to give rise to all differentiated cells provides a means of giving rise to any mammalian cells type, and so a range of culture conditions may be used to induce differentiation.

The relative term "differentiating" describes the active process whereby the cell is progressing down the developmental pathways to become more lineage restricted and mature.

Among the differentiated cells of interest are cells not readily grown from somatic stem cells, or cells that may be required in large numbers and hence are not readily produced in useful quantities by somatic stem cells.

Differentiated stem cells may express markers on their cell surface that may be indicative of a specific cell type, for example, indicative of cardiomyocytes. The markers may be used to identify and isolate the differentiated cardiomyocytes from other differentiated cells and undifferentiated stem cells.

By "markers", it is meant to refer to any moiety that can be used to identify the desired cardiomyocyte. For example, markers may be polypeptide molecules that are expressed on a cell of interest such as a "surface marker". The specific marker may be present only in the cells of interest, or encompass the cells of interest, or detectable level of the marker is sufficiently higher in the cells of interest, compared to other cells, such that the cells of interest can be identified, using any of a variety of methods as known in the art. It will be understood by those of skill in the art that expression is a relative term, and the expression will vary from other cell types. For example, a progenitor cell may express a polypeptide that is not found in the fully differentiated progeny cell. A cell of interest may express a polypeptide that is not expressed in surrounding tissues, e.g, the cardiomyocyte cells of fetal phenotype may express CD166 polypeptides not found in mature cardiomyocytes or on other cells of a non-cardiomyocyte lineage. This specificity is sufficient for purposes of cell identification and isolation.

By "cardiomyocyte", it is meant to refers to any cell in the cardiac myocyte lineage that shows at least one phenotypic characteristic of a cardiac muscle cell. Such phenotypic characteristics include expression of cardiac proteins, such as cardiac sarcomeric or myofibrillar proteins or atrial natriuretic factor, or electrophysiological characteristics. The term "cardiomyocyte" and "myocyte" are used interchangeably. In one example, a cardiomyocyte is defined as any cell in the cardiac myocyte lineage expressing cell surface markers CD200, JAK2, CD181 and CHRND. The cell may also express one or more additional markers (not necessary cell surface markers) including alpha-actinin, annexin, atrial natriuretic peptide (ANP), brain natriuretic peptides (BNP), cardiac troponin I (cTn1), cardiac troponin-T, caveolin-2, caveolin-3, connexin-43, dHAND, eHAND, GATA-4, myosin heavy chain, myosin light chain, Nkx2.5.

In a typical assay for detection and/or isolation, a heterogeneous population of differentiated stem cell is contacted with at least one a marker-specific "agent", and detecting directly or indirectly the presence of the complex formed.

Methods for isolating, and selecting, for cells based on expression of cell surface markers will be familiar to persons skilled in the art.

The isolated or selected cells to which the binding agent(s) is bound may then be isolated. Isolation of cells may be achieved by any of the methods known in the art, including affinity based interaction, affinity panning, magnetic beads (e.g. Dynabeads) or flow cytometry. The flow cytometry preferably employs a cell sorter so that the cells bearing surface markers CD200, JAK2, CD181 and CHRND (and therefore staining positive for CD200, JAK2, CD181 and CHRND) can be removed from cells that do not stain positive for these cell surface markers.

In one example, the cells are selected using the binding agents described herein, and optionally one or more other cell surface markers, and isolated using fluorescence activated cell sorting (FACS) or magnetic activated cell sorting (MACS™). In one example, the cells are selected using MACS™, where the cells are required for in vivo studies or in vivo administered compositions.

In another example, the cells may be isolated by binding to an immobilised support and then harvested by removing them from the support.

The harvesting of cells may be achieved by collecting the isolated cells into a suitable receptacle or collection dish, tube etc.

In various embodiments, the population of cells enriched for cardiomyocytes according to the methods using the surface markers disclosed herein are obtained. However, it is understood that the cells may comprise one or more additional cell surface markers, typically markers which are known to be expressed on cardiomyocytes.

In various embodiments, the method further comprises differentiating cardiomyocytes sub-types in the sample by contacting the sample with a first agent that specifically binds to a cell surface marker selected from Row A of Table 1 to provide a first population of ventricular cardiomyocytes and a second agent that specifically binds to a cell surface marker selected from Row B of Table 1 to provide a second population of atrial cardiomyocytes.

In various embodiments, the first and the second agents are the same. In other words, advantageously, a single agent may be used to distinguish between cardiomyocyte sub-types. For example, a single agent (such as an antibody) may be used to differentiate and separate between SIRPA+ ventricular and atrial cardiomyocytes, i.e. SIRPA+CD200+ cells are ventricular cardiomyocytes, while SIRPA+CD200− cells are atrial-like.

In other embodiments of the invention, the method further comprises the step of, prior to isolating the cardiomyocyte population, generating a culture of the sample and causing differentiation of the cells in the sample, i.e. providing a population of human pluripotent stem cells induced to differentiate into cardiomyocyte and then selecting for cells in the sample bearing the cell surface markers.

By "agent", it is meant to refer to any moiety capable of binding to another moiety, for example the marker on the cell surface, through chemical or physical means, wherein the agent and the marker forma binding pair. For example antibodies specific for these cell surface markers are commercially available, or may be produced using conventional methods as known in the art, therefore the antibodies and markers form a binding pair.

As such, in a various embodiments, the binding agent is an antibody or a fragment thereof. Exemplary antibodies are chimeric antibodies, humanized antibodies or human antibodies. The antibody may be produced recombinantly or by hybridoma generation according to standard techniques.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference. A fragment may contain one or more of the variable heavy (VH) or variable light (VL) domains. For example, the term antibody fragment includes Fab-like molecules (Better et al (1988) Science 240, 1041); Fv molecules (Skerra er al (1988) Science 240, 1038); single-chain Fv (ScFv) molecules where the VH and VL partner domains are linked via a flexible oligopeptide (Bird er al (1988) Science 242, 423; Huston et al (1988) Proc. Natl. Acad. Sci. USA 85, 5879) and single domain antibodies (dAbs) comprising isolated V domains (Ward et al (1989) Nature 341, 544). It also includes any "antibody variant" which means any synthetic antibodies, recombinant antibodies or antibody hybrids, such as but not limited to, a single-chain antibody molecule produced by phage-display of immunoglobulin light and/or heavy chain variable and/or constant regions, or other immune-interactive molecule capable of binding to an antigen in an immunoassay format that is known to those skilled in the art.

A general review of the techniques involved in the synthesis of antibody fragments which retain their specific binding sites is to be found in Winter & Milstein (1991) Nature 349, 293-299.

In various embodiments, it is possible for the binding agent to be an aptamer.

Molecular libraries such as antibody libraries (Clackson et al, 1991, Nature 352, 624-628; Marks ef al, 1991, J Mol Biol 222(3): 581-97), peptide libraries (Smith, 1985, Science 228(4705): 1315-7), expressed cDNA libraries (Santi et al (2000) J Mol Biol 296(2): 497-508), libraries on other scaffolds than the antibody framework such as affibodies (Gunneriusson ef al, 1999, Appl Environ Microbiol 65(9): 4134-40) or libraries based on aptamers (Kenan ef al, 1999, Methods Mol Biol 118, 217-31) may be used as a source from which binding agents that are specific for a given motif are selected for use in the methods of the present invention, particularly those that would adhere and bind to those protein biomarkers defined in Table 1.

The molecular libraries may be expressed in vivo in prokaryotic (Clackson ef al, 1991, op. c/f.; Marks ef al, 1991, op. cit.) or eukaryotic cells (Kieke ef al, 1999, Proc Natl Acad Sci USA, 96(10):5651-6) or may be expressed in vitro without involvement of cells (Hanes & Pluckthun, 1997, Proc Natl Acad Sci USA 94(10):4937-42; He & Taussig, 1997, Nucleic Acids Res 25(24):5132-4; Nemoto et al, 1997, FEBS Lett, 414(2):405-8). In cases when protein based libraries are used often the genes encoding the libraries of potential binding molecules are packaged in viruses and the potential binding molecule is displayed at the surface of the virus (Clackson ef al, 1991, op. cit; Marks ef al, 1991, op. cit; Smith, 1985, op. cit).

When potential binding molecules are selected from libraries one or a few selector peptides having defined motifs are usually employed. Amino acid residues that provide structure, decreasing flexibility in the peptide or charged, polar or hydrophobic side chains allowing interaction with the binding molecule may be used in the design of motifs for selector peptides.

The antibody or protein comprising an antibody variable region may be unconjugated or conjugated to a moiety. Examples of suitable moieties include biotin or a fluorescent label e.g. FITC. Any suitable label that facilitates the enrichment or detection of cardiomyocytes according to the invention is intended to be included within the scope of the present disclosure.

Thus, in various embodiments, the antibody is labelled with a detectable moiety. The detectable moiety may be selected from the group consisting of: a fluorescent moiety, a luminescent moiety, a chemiluminescent moiety, a radioactive moiety, an enzymatic moiety and a secondary anti-body. By a "detectable moiety", it is meant to include any moiety which may be detected and the relative amount and/or location of the moiety determined.

A detectable moiety may be a fluorescent and/or lumi-nescent and/or chemiluminescent moiety which, when exposed to specific conditions, may be detected. For example, a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes used may be those known for use in assays such as the ELISA.

Alternatively, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $^{17}$O, gadolinium, manganese or iron. Clearly, the agent to be detected (such as, for example, the one or more proteins in the test sample and/or control sample described herein and/or an antibody molecule for use in detecting a selected protein) must have sufficient of the appropriate atomic isotopes in order for the detectable moiety to be readily detectable.

The radio- or other labels may be incorporated into the agents of the invention (i.e. the proteins present in the samples of the methods of the invention and/or the binding agents of the invention) in known ways. For example, if the binding moiety is a polypeptide it may be biosynthesised or may be synthesised by chemical amino acid synthesis using suitable amino acid precursors involving, for example, fluo-rine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker of al (1978) Biochem. Biophys. Res. Comm. 80, 49-57) can be used to incorporate $^{123}$I. Reference ("Mono-clonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

It will be appreciated that the binding agents may be used simultaneously or sequentially. For example, the cells may be first selected on the basis of cell surface binding to CD200, JAK2, CD181 or CHRND and then isolated by flow cytometry and then further selected with a binding agent to another cell surface marker followed by further flow cytom-etry. Alternatively, the cells may be selected using binding agents simultaneously to all cell surface markers, wherein one of the binding agents may be labelled with e.g. FITC (fluorescein isothiocyanate) and the second binding agent labelled with e.g. phycoerythrin (PE) which facilitates iso-lation by flow cytometry.

According to the present invention, the cells selected according to the methods disclosed herein constitute a population of cells having at least about 50%, 55%, 60%, 65%, 70%, 75%, 80%, 85%, 87%, 90%, 95%, 96%, 97%, 98%, 99%, or 100% cardiomyocyte cells. In one example, the selected or isolated cells have at least about 70% cardiomyocytes. In another example, the selected or isolated cells have at least about 80% cardiomyocytes. In another example, the selected cells have at least about 90% cardio-myocytes.

The present invention also provides a population of cells enriched for cardiomyocytes according to a method described herein. In one example, the population of cells has at least about 70% cardiomyocytes. In another example, the population of cells has at least about 80% cardiomyocytes. In another example, the population of cells has at least about 90% cardiomyocytes.

In various embodiments, the isolated cells comprise a population of cells having at least about 85% cardiomyo-cytes.

In various embodiments, the present invention also may provide for a purified population of cells comprising at least about 50%, 55%, 60%, 65%, 70%, 75%, 80%. 85%, 87%, 90%, 95%, 96%, 97%, 98%, 99%, or 100%) cardiomyo-cytes. In other examples, the purified population of cells may comprise at least about 50%, 55%, 60%, 65%, 70%, 75%, 80%, 85%, 87%, 90%, 95%, 96%, 97%, 98%, 99%, or 100% cardiomyocytes having CD200, JAK2, CD181 and CHRND surface markers.

In various embodiments, the cardiomyocyte population is isolated using fluorescent activated cell sorting.

In various embodiments, the cells in the sample comprises cardiomyocytes differentiated from human pluripotent stem cells. The cells may be ES03 cells and/or BJ iPS cells.

In another aspect of the present invention, there is pro-vided a method for detecting cardiomyocytes in a sample, the method comprising: (a) contacting the sample with at least one binding agent that specifically binds to at least one cardiomyocyte surface marker, for a time and under condi-tions sufficient for the binding agent to bind, the cardiomyo-cyte surface marker is selected from the group consisting of: CD200, JAK2, CD181 and CHRND; and (b) isolating the cells bound to the binding agent, wherein the cells to which the binding agent bind are cardiomyocytes.

The cardiomyocytes are detected by immunohistochem-istry, and the sample is a mixed population of cells com-prising cardiomyocytes.

In another aspect of the present invention, there is pro-vided an isolated cardiomyocyte population that is isolated by the method of the present invention. In various embodi-ments, the isolated cardiomyocyte population may comprise at least 85% purity. By "purity", it is meant to refer to the specificity of those cell surface markers in Table 1 for isolating the respective ventricular and atrial specific car-diomyocytes.

In yet another aspect of the present invention, there is provided an isolated cardiomyocyte population for use in medicine. An isolated cardiomyocyte population of the present invention may be used in prevention, repair and/or treatment of at least one cardiac disorder in a subject. The cardiovascular diseases or disorders that are amenable to treatment include coronary heart disease; cardiomyopathy, endocarditis, congenital cardiovascular defects and conges-tive heart failure, long QT syndrome and other ion channel pathologies.

As such, in another aspect of the invention, there is provided a pharmaceutical composition comprising a thera-peutically effective amount of said population of cells, together with a pharmaceutically acceptable carrier.

In yet another aspect of the present invention, there is provided method for treating a subject suffering from a cardiovascular disease or disorder, comprising administer-ing to the subject a therapeutically effective amount of said isolated population of cells, or a pharmaceutical composition according to the present invention.

By "cardiovascular disease or disorder", it is meant to refer to a disease or disorder related to the cardiovascular or circulatory system. Cardiovascular disease and/or disorders include, but are not limited to, diseases and/or disorders of the pericardium, heart valves (i.e. incompetent valves, stenosed valves, rheumatic heart disease, mitral valve prolapse, aortic regurgitation), myocardium (coronary artery disease, myocardial infarction, heart failure, ischemic heart disease, angina). The person skilled in the art would be aware that cardiovascular diseases and/or disorders can result from congenital defects, environmental influences (i.e. dietary, lifestyle, stress etc) and other defects or influences.

The purified cardiomyocytes or pharmaceutical compositions disclosed herein may be surgically implanted, injected, delivered (e.g. by way of a catheter or syringe), or otherwise administered directly or indirectly to the site in need of repair or augmentation. Exemplary routes of parenteral administration include intravenous, intra-arterial, intramuscular, intraperitoneal, intramyocardial, transendocardial, transepicardial, intranasal or intrathecal, and infusion techniques.

Intra-arterial administration includes delivery into an aorta, into an atrium or ventricle of the heart or into a blood vessel. In the case of cell delivery to an atrium or ventricle of the heart, cells can be administered to the left atrium or ventricle to avoid complications that may arise from rapid delivery of cells to the lungs.

In another aspect of the invention, the identified, isolated, enriched and purified cardiomyocytes or compositions disclosed herein may optionally be packaged in a suitable container with written instructions for a desired purpose, such as the reconstitution of cardiomyocyte cell function to improve some abnormality of the cardiac muscle or for use in screening or diagnostic applications.

In addition, the purified cardiomyocytes can also be used to generate engineered heart tissues or patches for transplantation onto an infarcted heart, drug screening or cardiotoxicity test, organ-on-chip, etc.

The invention thus provides for a kit comprising at least one binding agent which binds to a cardiomyocyte surface marker, the cardiomyocyte surface marker is selected from Table 1, together with instructions for use in isolating or enriching cardiomyocytes. The components of the kit may be packaged with in aqueous media or in lyophilised form. The kit will typically also contain instructions for use.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Advantageously, utilizing the Method for Analyzing RNA following Intracellular Sorting (MARIS), reported by Hrvatin et al. (2014), the present invention has isolated atrial and ventricular cardiomyocytes based on known intracellular markers, MLC2a and MLC2v, respectively. The isolation of both atrial and ventricular cardiomyocytes were performed on cells derived from two human pluripotent stem cells (ES03 and BJ iPS). The cardiomyocytes samples were then prepared for RNA sequencing. The analysis from the RNA sequencing data revealed potential surface markers that can be utilised for the purification of specific cardiomyocyte sub-types.

As used herein, the term "specifically binds" shall be taken to mean that the binding agent e.g. antibody or protein comprising an antibody variable region reacts or associates more frequently, more rapidly, with greater duration and/or with greater affinity with a particular cell or substance than it does with alternative cells or substances. For example, a binding agent that specifically binds to a target protein is an agent that binds that protein or an epitope or immunogenic fragment thereof with greater affinity, avidity, more readily, and/or with greater duration than it binds to unrelated protein and/or epitopes or immunogenic fragments thereof. It is also understood by reading this definition that, for example, a binding agent that specifically binds to a first target may or may not specifically bind to a second target. As such, "specific binding" does not necessarily require exclusive binding or non-detectable binding of another molecule, this is encompassed by the term "selective binding". Generally, but not necessarily, reference to binding means specific binding.

As used herein, the term "subject" shall be taken to mean any subject, including a human or non-human subject. The non-human subject may include non-human primates, ungulate (bovines, porcines, ovines, caprines, equines, buffalo and bison), canine, feline, lagomorph (rabbits, hares and pikas), rodent (mouse, rat, guinea pig, hamster and gerbil), avian, and fish. In one example, the subject is a human.

As used herein, the term "therapeutically effective amount" shall be taken to mean a sufficient quantity of a population of cells enriched for cardiomyocytes obtained from the present methods, or otherwise isolated and purified cells obtained by the present methods that result in an improvement or remediation of the symptoms of the disease or condition. The skilled artisan will be aware that such an amount will vary depending upon, for example, the particular subject and/or the type or severity or level of disease. The term is not to be construed to limit the present disclosure to a specific quantity, e.g. weight or number of cells, rather the present disclosure encompasses any number of cells sufficient to achieve the stated result in a subject.

As used herein, the terms "treating", "treat" or "treatment" include administering a therapeutically effective amount of a population of cells enriched for cardiomyocytes or otherwise isolated and purified cells or a composition comprising such cells described herein sufficient to reduce or eliminate at least one symptom of a specified disease or condition.

The terms "enriched", "enrichment" or variations thereof are used herein to describe a population of cells in which the proportion, or percentage of cells of one particular cell type or the proportion or percentage of a number of particular cell types is increased when compared with an untreated population of the cells (e.g. cells in their native environment).

In one example, the term "enriched" is taken to mean that the proportion or percentage of cardiomyocytes is greater than the proportion or percentage of cardiomyocytes in the population of cells from which it was originally contained.

In order that the present invention may be fully understood and readily put into practical effect, there shall now be described by way of non-limitative examples only preferred embodiments of the present invention, the description being with reference to the accompanying illustrative figures.

IN THE FIGURES

FIG. 1. Heterogeneity in cardiomyocytes derived from directed differentiation of human pluripotent stem cells (PSCs)

(a) Schematic illustration of GiWi differentiation protocol that generates different populations of atrial-like, ventricular-like and pacemaker-like cardiomyocytes. (b) Representative FACS plots illustrating purification of SIRPA+ PSC derived cardiomyocytes. Graphical representation of the percentage of SIRPA+ cardiomyocytes generated from ES03 and BJ iPS cells, respectively. (c) Representative images of cardiomyocytes immunostained for cTnT (green). Cell nuclei (blue) were stained with DAPI. Scale bar, 100 μm.

Figure 2:
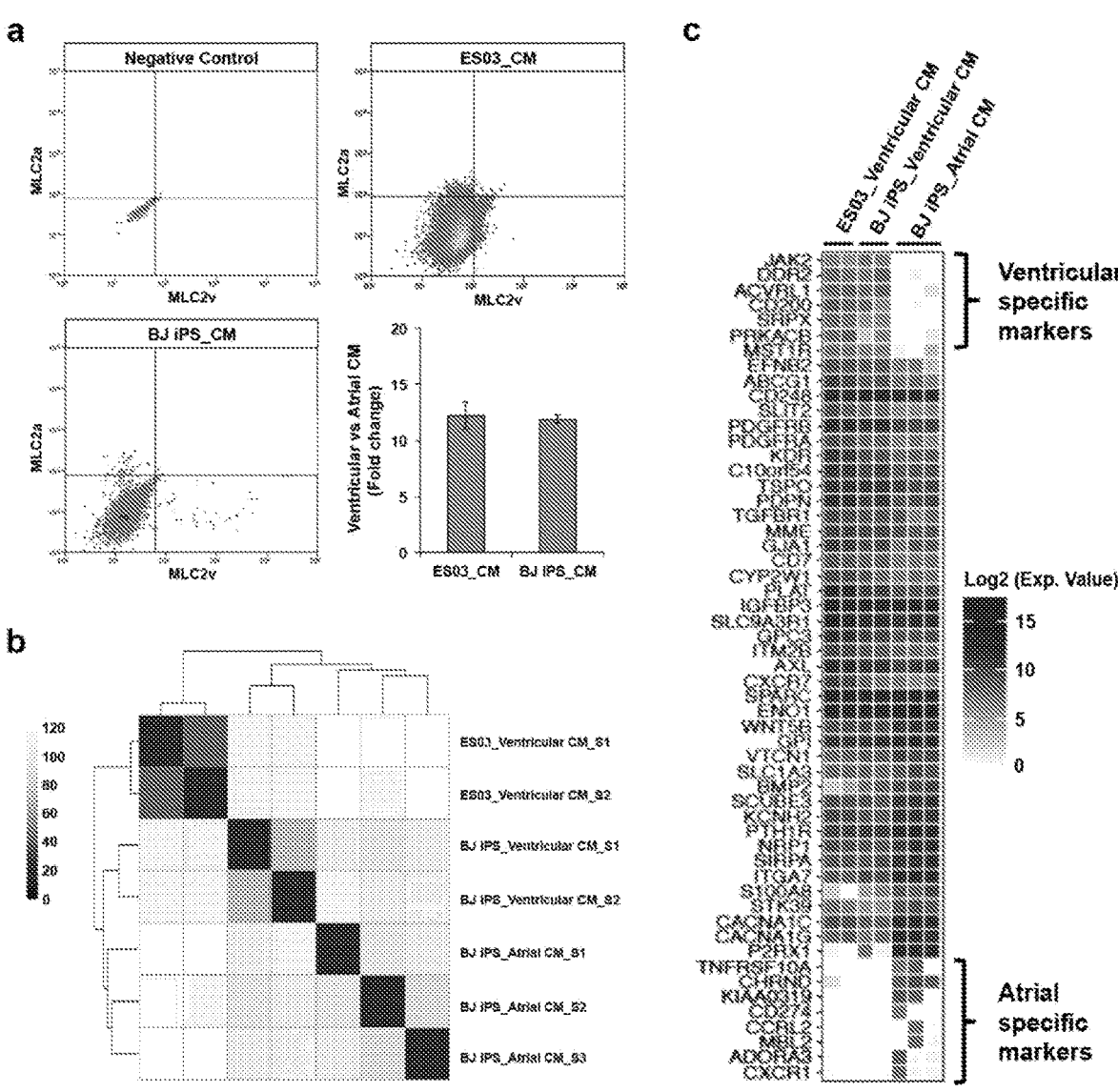

FIG. 2. Identification of atrial and ventricular specific cell surface markers via *MARIS* method (a) Representative FACS plots illustrating purification of MLC2v and MLC2a PSC derived cardiomyocytes. Graphical representation illustrating fold change of ventricular cardiomyocytes versus atrial cardiomyocytes obtained from differentiation of ES03 or BJ iPS cells. Error bars indicate s.d, n=3 experiments. *P<0.05 and ** P<0.01; evaluated by Student's t-test. (b) Heat map illustrating clustering of biological replicates within the same group. (c) Heat map showing 50 differentially expressed cell surface genes.

Figure 3:
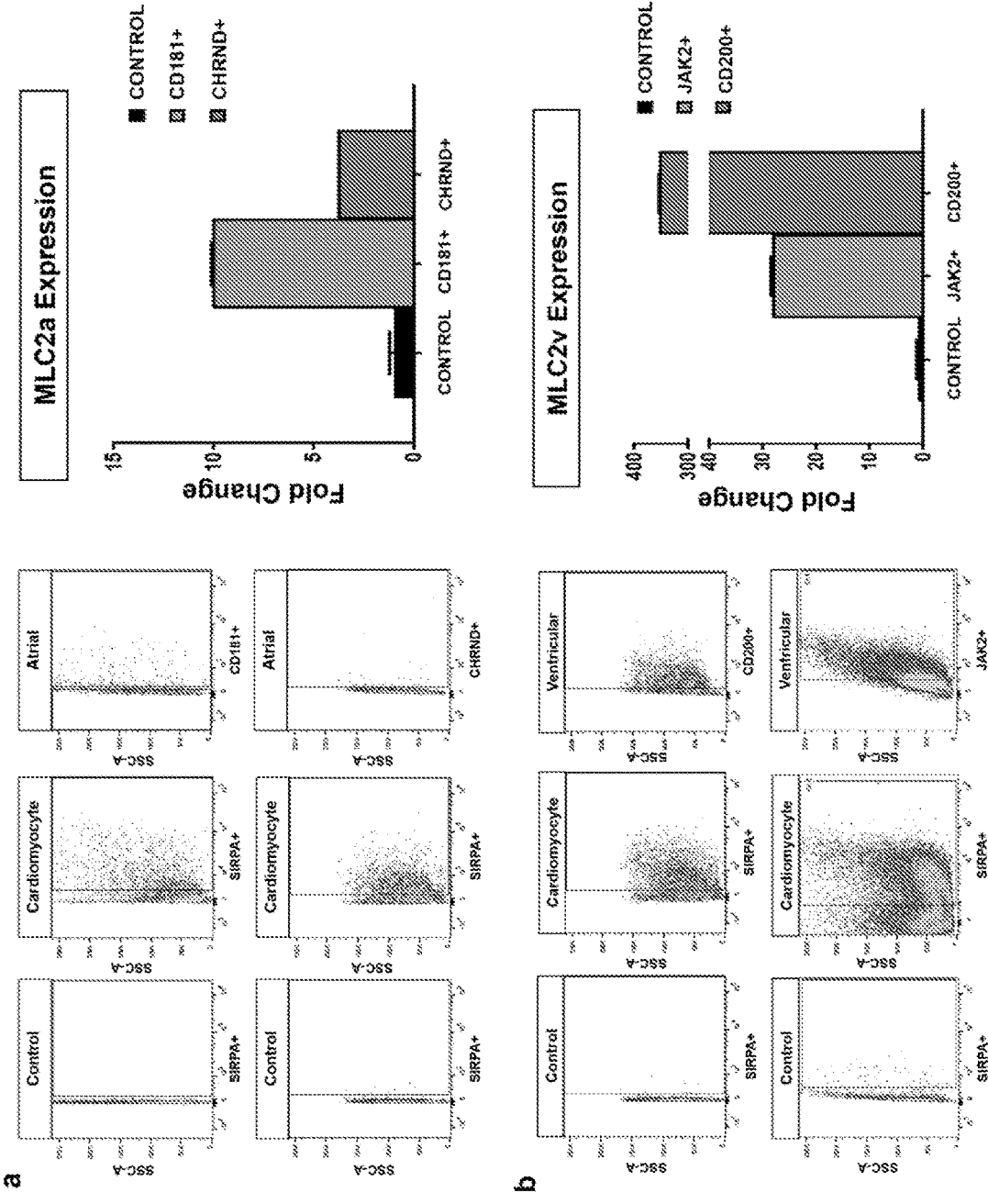

FIG. 3. Validating specific cell surface markers for purification of cardiomyocytes sub-populations (a) Representative FACS plots (left panel) illustrating purification of atrial cardiomyocytes using SIRPA+/CD181+ and SIRPA+/CHRND+ antibodies, respectively. Graphical representation showing qPCR data on MLC2a expression illustrates enrichment in atrial cardiomyocyte population (right panel). Error bars indicate s.d, n=3 experiments. *P<0.05 and ** P<0.01; evaluated by Student's t-test. (b) FACS plots illustrating ventricular cardiomyocytes purification using SIRPA+/CD200+ and SIRPA+/JAK2+ antibodies were shown in the left panel. Quantitative PCR was performed on these isolated cardiomyocytes demonstrating significant up-regulation of ventricular specific (MLC2v) gene. Error bars indicate s.d, n=3 experiments. *P<0.05 and ** P<0.01; evaluated by Student's t-test.

Figure 4:
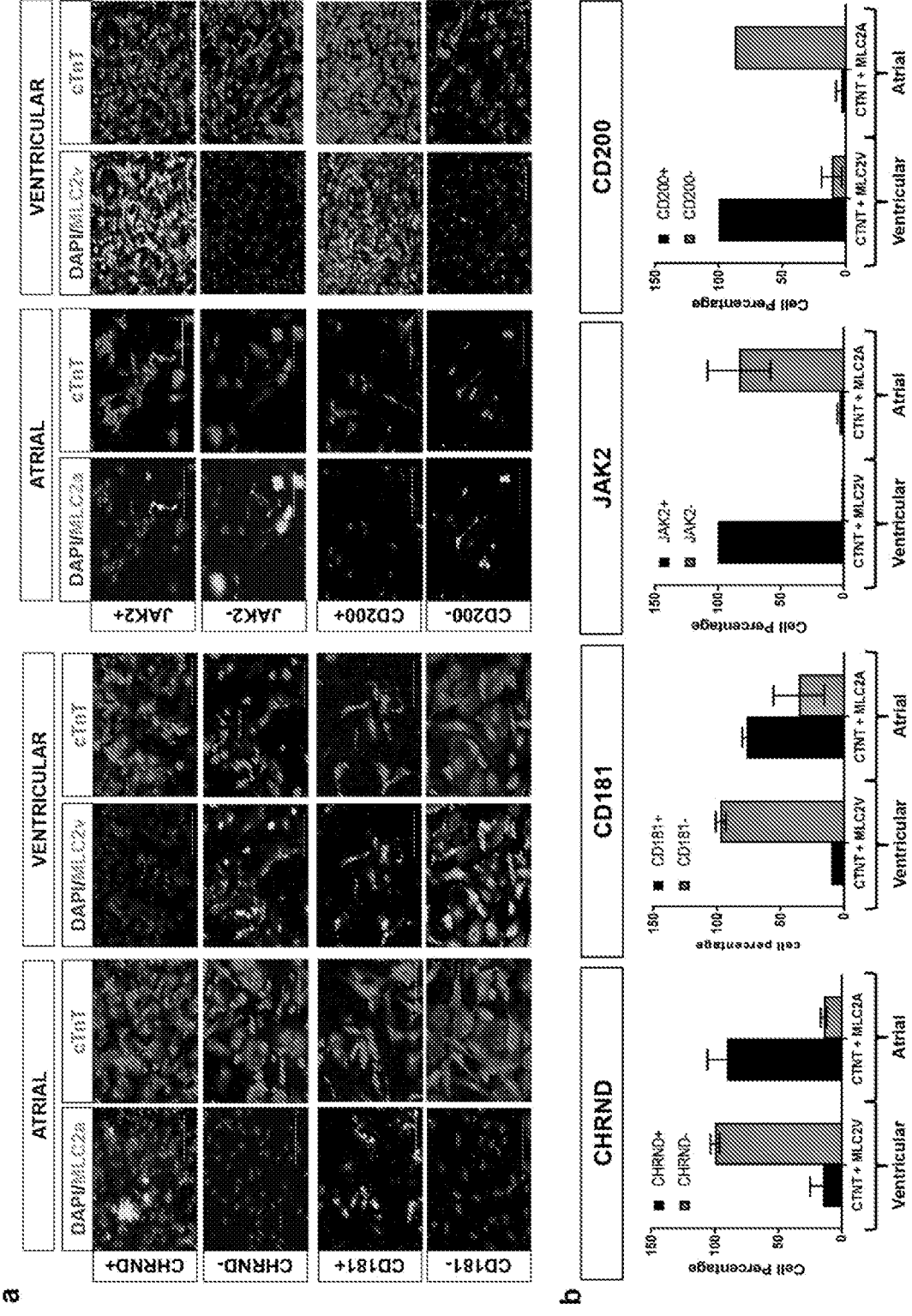

FIG. 4. Efficient purification of cardiomyocyte sub-populations using a single cell surface marker.

(a) Immunocytochemistry of purified cardiomyocytes using atrial (CD181, CHRND) or ventricular (CD200, Jak2) specific antibodies, coupled with SIRPA antibody. From the results, it is evident that SIRPA+/CHRND+, SIRPA+/JAK2– and SIRPA+/CD200– enriched for atrial cardiomyocytes, with more than 85% of the sorted cardiomyocytes being positive for MLC2a. Conversely, SIRPA+/CHRND–, SIRPA+/JAK2+ and SIRPA+/CD200+ resulted in the enrichment of ventricular cardiomyocytes with >90% purity. CD181, the other hand, was not as efficient since a considerable amount of SIRPA+/CD181+ cardiomyocytes (~30%) are also stained positive for MLC2v, a ventricular marker. (b) Graphical representations of the cell proportion of atrial (CTNT+MLC2A) and ventricular (CTNT+MLC2V) cardiomyocytes purified by various antibodies identified in this study (CHRND, CD181, JAK2, CD200). Error bars indicate s.d, n=3 experiments. * P<0.05 and ** P<0.01 for Kruskal-Wallis one-way analysis of variance compared to control.

EXAMPLE 1

Materials and Methods

1. Cell Culture of Human ES and iPS Cells for Differentiation Towards Cardiomyocytes The present invention relied on a protocol set out in Lian, X. et al. (2013) Nature protocols 8, 162-175, doi:10.1038/nprot.2012.150, contents of which are incorporated by reference here.

The human ESC lines (ES03 and BJ iPS) were cultured in feeder-free condition on Matrigel (Corning, 354248). The cells were maintained in iPS-brew medium (Miltenyi, 130-104-368), and passaged with collagenase IV (1 mg/ml) (Gibco, 17104019) enzymatic treatment. To differentiate human ES cells towards cardiomyocytes, we adopted the protocol established by Lian et al[3,4]. In this study, hPSC derived cardiomyocytes were cultured until initial contraction before harvesting for analysis.

(a). Seeding of Human ES Cell for Cardiomyocyte Differentiation

1. ES cells were cultured on a 6-well plate in iPSC-Brew (Miltenyi Biotech, StemMACS™ iPS-Brew XF, human; catalog #130-104-368) to 80-90% confluency.

2. The medium was aspirated and washed with PBS (Gibco; cat #20012-027), twice.

3. 0.5 ml of accutase (Innovative cell technologies; cat #12679-54) was added to each well and incubated at 37° C. for 3-5 min to achieve single cell suspension (tapping of the plate is required periodically).

4. 2 ml of PBS was added into each well to dilute the accutase and wash out the cells. The cell suspension was then collected in a 15 ml falcon tube and centrifuge at 1200 rpm for 5 min to obtain the cell pellet.

5. The cell pellet was then resuspended in 18 ml of iPSC-Brew supplemented with 5 μM of Y27632.

NB: The starting seeding cell density is very critical for efficient cardiac differentiation. The initial plating density and/or the time of expansion prior to initiation of differentiation may require optimization for different cell lines or expansion conditions. (This time point corresponds to day −4).

6. On day −3, day −2, and day −1, the medium aspirated and replaced with 2 ml room temperature iPSC-Brew per well of the 6-well plate.

CRITICAL STEP: Ensure that the cells are 85-90% confluent on day 0 of differentiation.

(b). Differentiation of Human ES Cells Towards Cardiomyocytes

1. Day 0: 12 μM CHIR99021 (Miltenyi Biotech; cat #130-103-926) in RPMI-1640 medium (Hyclone: cat #SH30027.01)+B27-insulin (Gibco: cat #A1895601) was prepared. 3 ml RPMI/B27-insulin supplemented with CHIR99021 was added into each well of a 6-well plate. Cells were incubated at 37° C., 5% $CO_2$ for 1 days.

2. Day 1: The medium was aspirated from each well of the 6-well plate and replaced with 3 ml room temperature RPMI/B27-insulin (without CHIR99021). Cells were incubated at 37° C., 5% $CO_2$ for 2 days.

NB: Top up medium if a lot of cell death is observed (depending on cell lines)

3. Day 3: 5 μM IWP-2 (Miltenyi Biotech; cat #130-105-027) in RPMI/B27-insulin was prepared. 3 ml of RPMI/B27-insulin supplemented with IWP-2 was added into each well of the 6-well plate. Cells were incubated at 37° C., 5% $CO_2$ for 2 days.

4. Day 5: The medium was aspirated from each well of the 6-well plate and replaced with 3 ml of RPMI/B27-insulin (without IWP-2). Cells were incubated at 37° C., 5% $CO_2$ for 2 days.

NB: Top up medium if a lot of cell death is observed (depending on cell lines)

5. On day 7, the medium was aspirated from each well of the 6-well plate, replaced with 3 ml of RPMI/Neurobrew-21 (Miltenyi Biotech; cat #130-093-566). Cells were incubated at 37° C., 5% $CO_2$ thereafter.

2. Isolation of Human ES Cell Derived Cardiomyocyte

Human PSC-derived cardiomyocytes were washed with phosphate-buffered saline (PBS) (Gibco, 20012027) and incubated with accutase (Bio Laboratories, A1110501) at 37° C. for 5 mins to obtain a single-cell suspension. Cells were co-stained or tripled stained to isolate SIPRA+ atrial-specific cardiomycytes or SIRPA+ ventricle-specific cardio-myocytes. To isolate pure cardiomyocytes, the cells were stained with SIRPα/β PE-cy7 (Biolegend, 323808) or SIRPα/β PE (Miltenyi Biotech, 130-099-783) antibodies. Subsequently, isolation of SIRPA+ atrial-specific cardio-myocytes was done with CD181-APC (Miltenyi Biotech, 130-115-949) or CHRND (Invitrogen, PA5-71562) antibod-ies, while isolation of SIRPA+ ventricle-specific cardiomyo-cytes was done with CD200-VioBright FITC (Miltenyi Biotech, 130-106-064) or JAK2 (Life Technologies, PA511267) antibodies. For unconjugated CHRND and JAK2 antibody, a secondary staining was followed up using donkey anti-rabbit IgG alexa fluor 594 (Invitrogen, A21207) or 488 (Invitrogen, A21206) respectively at 1:1000 dilution for 1 hour. SIRPα/β PE-cy7, SIRPα/β PE, CD181-APC and CD200-VioBright FITC staining was done at 1:150 dilu-tions, while CHRND and JAK2 staining was done at a 1:60 dilution. All staining was conducted in blocking buffer consisting of 5% fetal *bovine serum* (FBS) (Hyclone, sv30160.03) and 2% *Bovine Serum Albumin* (BSA) (GE Healthcare K41-001) in PBS for 90 mins at 37° C. Stained cardiomyocytes were subsequently purified via FACs with BD FACSAria™ II system.

Binding Agents

The binding agents according to the present disclosure may be non-antibody based binding agents or antibodies or proteins containing an antibody variable region.

Typical non-antibody based binding agents include pep-tides, peptidomimetics, nucleic acid aptamers, peptide aptamers, dendrimers and small organic molecules.

A nucleic add aptamer (adaptable oligomer) is a nucleic acid molecule that is capable of forming a secondary and/or tertiary structure that provides the ability to bind to a molecular target. An aptamer library is produced, for example, by cloning random oligonucleotides into a vector (or an expression vector in the case of an RNA aptamer), wherein the random sequence is flanked by known sequences that provide the site of binding for PCR primers. An aptamer with increased activity is selected, for example, using SELEX (Sytematic Evolution of Ligands by Expo-nential enrichment), Suitable methods for producing and/or screening an aptamer library are described, for example, in Elloington and Szostak, Nature 346:818-22, 1990.

Techniques for synthesizing small organic compounds will vary considerably depending upon the compound, how-ever such methods will be well known to those skilled in the art. In one embodiment, informatics is used to select suitable chemical building blocks from known compounds, for pro-ducing a combinatorial library. For example, QSAR (Quan-titative Structure Activity Relationship) modelling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead com-pounds. The Binary QSAR method is based upon three characteristic properties of compounds that form a "descrip-tor" of the likelihood that a particular compound will or will not perform a required function: partial charge, molar refrac-tivity (bonding interactions), and log P (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens can be used to expand the list of compounds being screened to thereby identify highly active compounds.

Particularly preferred binding agents are antibodies or antigen binding fragments thereof or proteins comprising an antibody variable region. As used herein the term "antibody" refers to an immunoglobulin molecule capable of binding to a target, such as CD200, JAK2, CD181 or CHRND and/or an epitope thereof and/or an immunogenic fragment thereof and/or a modified form thereof (e.g., glycosylated) through at least one epitope recognition site, located in the variable region of the immunoglobulin molecule. This term encom-passes not only intact polyclonal or monoclonal antibodies, but also variants, fusion proteins comprising an antibody portion with an epitope recognition site of the required specificity, humanized antibodies, human antibodies, chime-ric antibodies, and any other modified configuration of the immunoglobulin molecule that comprises an epitope recog-nition site of the required specificity.

The term "antigen binding fragment" or "protein com-prising an antibody variable region" shall be taken to mean any fragment of an antibody that retains the ability to bind to a target, such as CD200, JAK2, CD181 or CHRND. Such fragments typically include Fab, Fab', $(Fab')_2$, Fv, single chain antibody (e.g. scFv), single domain antibody (e.g. dAb). Methods of making these fragments are known in the art. See for example, Harlow and Lane, Antibodies: A Laboratory Manual, Cold Spring Harbour Laboratory, New York (1988), incorporated herein by reference.

The term "monoclonal antibody" refers to a homogeneous antibody population capable of binding to the same antigen(s) and, preferably, to the same epitopic determinant within the antigen(s). This term is not intended to be limited as regards to the source of the antibody or the manner in which it is made.

The term "chimeric antibody" refers to antibodies in which a portion of the heavy and/or light chain is identical with or homologous to corresponding sequences in antibod-ies derived from a particular species (e.g., murine, such as mouse) or belonging to a particular antibody class or sub-class, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816,567; and Morrison et al. (1984) Proc. Natl Acad. Sci USA 87:6851-6855).

The term "humanized antibody" shall be understood to refer to a chimeric molecule, generally prepared using recombinant techniques, having an epitope binding site derived from an immunoglobulin from a non-human species and the remaining immunoglobulin structure of the molecule based upon the structure and/or sequence of a human immunoglobulin. The antigen-binding site preferably com-prises the complementarity determining regions (CDRs) from the non-human antibody grafted onto appropriate framework regions in the variable domains of human anti-bodies and the remaining regions from a human antibody. Epitope binding sites may be wild type or modified by one or more amino acid substitutions. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When non-human antibodies are prepared with respect to a particular epitope, the variable regions can be "reshaped" or "human-ized" by grafting CDRs derived from nonhuman antibody on the FRs present in the human antibody to be modified. Application of this approach is known in the art.

4. Immunocytochemistry

Immunocytochemical analysis was performed using the respective antibodies: mouse anti-cardiac troponin T (Ab-cam, ab8295), MLC2a (Zuellig Pharma, 565496) and MLC2v (Zuellig Pharma, 565497) at manufacturer's recom-mended dilutions. Briefly, cells were first harvested and washed once with PBS. Fixation of cells was achieved with 4% paraformaldehyde (Axil Scientific, 09154-56) for 30 minutes, followed by permeabilization with 0.2% Triton X (Bio-Rad, 161-0407), if necessary. The cells were then blocked with 5% FBS and 1% BSA in PBS for 30 mins at room temperature. Primary antibodies were added at respec-tive dilutions and incubated at 4° C. overnight. After wash-ing once with PBS, the cells were incubated in the dark with either 1:1000 diluted Alexa Fluor 488 (Invitrogen, A21206) or Alexa Fluor 594 (Invitrogen, A21207) secondary anti-bodies for 60 mins at room temperature. Nuclei were coun-terstained with 4,6-diamindino-2-phenylindole (DAPI) (AAT Bio, 17510). The cells were observed under a fluo-rescent microscope (Nikon TS-100) and imaged with Olym-pus fluoview FV1000 confocal microscope.

5. RNA Isolation and Quantitative PCR

For cultured cell samples, $2 \times 10^6$ cells were harvested and lysed in 800 µl of TRIzol reagent (Life Technologies, 10296028). The samples were allowed to stand for 5 mins at room temperature, after which 160 µl of chlorofoam (Kento Chemicals, 07278-00) was added. Phase separation was achieved by centrifugation at 12,000×g for 15 mins at 4° C. Following that, the aqueous phase was transferred to a clean 1.5 ml Eppendorf tube. Equal volume of isopropanol (Merck, 67-63-0) was added and the RNA samples were allowed to precipitate at room temperature for another 10 mins. The precipitated RNA samples were pelleted by centrifugation at 12,000×g for 15 min at 4° C. For cDNA synthesis, RNA samples (500 ng) were reverse transcribed to obtain cDNA using High-Capacity cDNA Reverse Tran-scription Kit (Applied Biosystems, 4368813). Primer sequences are provided in Supplementary Table 1. Quanti-tative PCR (qPCR) analyses were performed using SYBR Green Master Mix Reagent (Applied Biosystems, 4385614) on an ABI Viia7 Real Time PCR System. The threshold cycle (Ct) was determined to be Each experiment was repeated at least twice. Standard deviations (s.d.) of the means in qPCR experiments were obtained from three independent experiments.

6. Statistics

Quantitative PCR values are expressed as mean±s.d. results were tested for statistical significance using Student's t-test, two sided based on assumed normal distributions. p values <0.05 were considered statistically significant.

Results and Discussion

1. Heterogeneity in Cardiomyocytes Derived from Directed Differentiation of Human Pluripotent Stem Cells (hPSCs)

Earlier reports have demonstrated the efficiency and reproducibility of directed differentiation of human pluripotent stem cells (hPSC) and embryonic stem cells (ESC) as an approach to derive patient specific cardiovascular cells. Studies modeling aspects of cardiovascular disease have shown to be critical in studying heart development by constructing disease models and drug screening tools on specific cell types in vitro. In this study, using previously published protocol reported by Lian et al. [3,4], we generated cardiomyocytes consisting of varying cardiomyocyte cell types such as atrial, ventricular and pacemaker cells (FIG. 1a). For the purpose of our study, cardiomyocytes were cultured till initial contraction, after which fluorescent acti-vated cell sorting (FACS) was performed to purifiy cardio-myocytes based on SIRPA α/β expression, a cardiomyocyte specific marker (FIG. 1b). From the results (FIG. 1b, c), it is evident that while the GiWi method of directed cardio-myocyte differentiation achieved 36% and 32% SIRPA+ cardiomyocytes from ES03 and BJ iPS cells, respectively, a minority of the sorted cells is cardiac troponin T (cTnT) negative, suggesting that SIRPA may potentially stain for early cardiomyocyte precursor as well. In addition, gene expression analysis on SIRPA+ cells revealed heterogeneity in purified cardiomyocytes as markers such as MLC2a and MLC2v, specific for either atrial or ventricular cardiomyo-cytes were both up-regulated (FIG. 1d).

2. Identification of Atrial and Ventricular Specific Cell Surface Markers Via MARIS Method Herein, we showed through Fluorescence activated cell sorting (FACS), when co-stained for MLC2a and MLC2v intracellular markers that both ES03 and BJ derived cardio-myocytes in vitro consists of a varying cell types, such as atrial and ventricular cells (FIG. 2a). It is estimated from FACS data that the fold change in enrichment of ventricular versus atrial cardiomyocytes were approximately 12.5 and 11.5, respectively, suggesting the GiWi method of directed differentiation results in a higher population of ventricular cells compared to atrial cells. To facilitate the identification of cell surface markers, we adopted the MARIS (Method for Analysis of RNA following Intracellular Sorting) tech-nique[5], followed by RNA sequencing. Transcriptome pro-files for both atrial and ventricular cardiomyocytes were obtained and the top 50 differentially expressed cell surface markers were identified (FIG. 2b, c). The cell surface markers in Table 1 are obtained from FIG. 2(c).

3. Validating Specific Cell Surface Markers for Purification of Cardiomyocytes Sub-Population To validate the list of cell surface markers identified through our bioinformatics analysis, we tested some of the markers that were exclusively expressed on either atrial such as CXCR1 (also known as CD181) and CHRND (FIG. 3a), or ventricular cardiomyocytes such as CD200 and Jak2 (FIG. 2c).

For this purpose, we isolated SIRPA+ cells using FACS, followed by selecting for atrial-specific cardiomyocytes based on the expression of CD181 and CHRND cell surface markers, respectively (FIG. 3a). The population of CD181 positive and CHRND positive cardiomyocytes was further validated with quantitative polymerase chain reaction (qPCR). As expected, transcript profile analysis showed that enriched population of CD181 and CHRND positive car-diomyocytes exhibit significantly higher expression of atrial-specific genes (MYL7, also known as MLC2a), as compared to unsorted population of cardiomyocytes (FIG. 3a).

Likewise, to further test the ability to isolated ventricular-specific cardiomyocytes, we isolated SIRPA+ cells using FACS, followed by sequential isolation of cardiomyocytes expressing CD200 and JAK2 (FIG. 3b). We demonstrated that both CD200 and Jak2 were specific markers for ventricular cardiomyocytes, which were further validated using qPCR analysis, showing either CD200 or JAK2 positive cardiomyocytes exhibiting significantly higher level of MYL2 gene (also known as MLC2v) as compared to unsorted population of cardiomyocytes (FIG. 3b). These results further support our RNA sequencing data in FIG. 2, in which CD181 and CHRND are exclusively expressed in atrial cardiomyocytes, while CD200 and JAK2 are exclusively expressed in ventricular cardiomyocytes only.

To further validate that the shortlisted cell surface markers are specific for isolation and immunocytochemistry of cardiomyoyctes sub-populations (atrial or ventricular), we performed immunostaining illustrating MLC2a (atrial) and MLC2v (ventricular) expressions using cardiomyocytes (SIRPA positive) that were either positive/negative for CHRND, CD181, JAK2 or CD200. The results in FIG. 4 demonstrated that a single antibody (either CHRND, CD200 or JAK2), coupled with SIRPA was able to enrich for either atrial or ventricular cardiomyocytes. From the data, it is evident that SIRPA+/CHRND+, SIRPA+/JAK2– and SIRPA+/CD200– enriched for atrial cardiomyoyctes, with more than 85% of the sorted cardiomyocytes being positive for MLC2a. Conversely, SIRPA+/CHRND–, SIRPA+/JAK2+ and SIRPA+/CD200+ resulted in the enrichment of ventricular cardiomyocytes with >90% purity. CD181, the other hand, may not be a good surface marker to distinguish between atrial or venticular cardiomyoyctes as SIRPA+/CD181+ was stained positive for both MLC2a and MLC2v (FIG. 4).

4. Therapeutic Use

The present invention also provides for the use of the cardiomyocyte cells of the invention to enhance tissue maintenance or repair of cardiac muscle in a human patient or other subject in need of such treatment.

To determine the suitability of cell compositions for therapeutic administration, the cells are first tested in an animal model. The cells can be administered to immunodeficient animals. Tissues are harvested after a period of regrowth, and assessed as to whether they are still present. The cells can be labelled with a detectable label e.g. green fluorescent protein. The presence of the administered cells can be assessed by immunohistochemistry or ELISA.

Suitability can be determined by assessing the degree of cardiac recuperation that ensures from treatment of the cells of the invention. For example, hearts can be cryoinjured by placing a placing a precooled aluminium rod in contact with the surface of the anterior left ventricle wall, or by placing a 30-50 mm copper disk probe cooled in liquid nitrogen on the anterior wall of the left ventricle. Infarction can be induced by ligating the left main coronary artery. Injured sites are treated with cell preparations of this disclosure and the heart tissue examined by histology for the presence of the cells in the damaged area. Cardiac function can be monitored by determining such parameters as left ventricular end diastolic pressure, developed pressure, rate of pressure rise, and rate of pressure decay.

The cardiomyocyte cells of the present invention can be used for tissue reconstitution or regeneration in a human subject or other subject by administering in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location. The cells may be administered to a recipient heart by intracoronary injection, e.g. into the coronary circulation. The cells may also be administered by intramuscular injection into the wall of the heart. Cardiomyocytes can be administered as cell suspension or in the form of engineered heart tissue/patch using heart chamber specific cardiomyocytes. (Refer to comment [4] for other potential applications)

Subjects which are suitable candidates for treatment according to the methods of the present disclosure include those with acute or chronic heart conditions of various kinds, including coronary heart disease, cardiomyopathy, endocarditis, congenital cardiovascular defects and congestive heart failure.

In one example, the enriched cardiomyocyte cells of the present disclosure are administered to a subject suffering from myocardial infarction. For example, the injected cells migrate to the infracted myocardium. The cardiomyocytes assemble into myocardium tissue resulting in repair or regeneration of the infracted myocardium.

In another example, the enriched cardiomyocyte cells of the present disclosure are administered to a subject suffering from heart failure, wherein the mount is effective in at least partially restoring cardiac function. Heart failure can be considered as a progressive disease of apoptotically-mediated cardiomyocyte loss that eventually results in an impaired functional capacity of the cardiac muscle.

Efficacy of treatment can be monitored by clinically accepted criteria, such as reduction in area occupied by scar tissue or revascularisation of scar tissue, and in the frequency and severity of angina; or an improvement in developed pressure, systolic pressure, end diastolic pressure, $\Delta$pressure/$\Delta$time, ejection fraction, patient mobility and quality of life.

Treatment of subjects with enriched cell population of the present invention according to any of the above described methods may be used in conjunction with other procedures such as surgery.

5. Pharmaceutical Compositions

The purified cardiomyocyte cells of the present disclosure can be supplied in the form of a pharmaceutical composition, comprising a carrier or excipient. The choice of excipient or other elements of the composition can be adapted in accordance with the route and device used for administration.

The terms "carrier" and "excipient" refer to compositions of matter that are conventionally used in the art to facilitate the storage, administration, and/or the biological activity of an active compound (see, e.g. Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

The carrier or excipient can be a solvent or dispersion medium containing, for example, water, ethanol, polyol (i. e. glycerol, propylene, glycol and liquid polyethylene glycol and the like), suitable mixtures thereof and/or vegetable oils. The prevention of the action of microorganisms can be brought about by various antibacterial and antifungal agents, for example, parabens, chlorobutanol, phenol, sorbic acid, thimerosal and the like. It may also be preferable to include isotonic agents e.g. sugars or sodium chloride. Stabilising agents can also be added to protect the composition from loss of therapeutic activity. Examples include buffers, amino acids e.g. lysine, carbohydrates such as dextrose, mannose, galactose, fructose, lactose, sucrose, maltose, sorbitol, mannitol etc.

In another example, a carrier is a media composition, e.g., in which a cell is grown or suspended. For example, such a media composition does not induce any adverse effects in a subject to whom it is administered.

Exemplary carriers and excipients do not adversely affect the viability of a cell and/or the ability of a cell to function as a cardiomyocyte.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

The composition may also comprises or be accompanied with one or more other ingredients that facilitate the engraftment or functional mobilisation of the cells. Suitable ingredients include matrix proteins or gel polymer that support or promote adhesion of the cells or complementary cell types, especially endothelial cells.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, e.g., as described by Vacanti, et al, J. Ped. Surg. 23:3-9 1988; Cima, et al. Biotechnol. Bioeng. 38: 145 1991; Vacanti, et al. Plast. Reconstr. Surg. 88:753-9 1991; or synthetic polymers such as polyanhydrides, polyorthoesters, and polylactic acid.

In another example, the cells may be administered in a gel scaffold (such as Gelfoam from Upjohn Company.

The purified cardiomyocyte cells can be combined with the carrier or excipient in any convenient or practical manner e.g. suspension, emulsification, admixture, encapsulation, absorption and the like.

The compositions described herein may be administered alone or as admixtures with other cells. Cells that may be administered in conjunction with the compositions of the present disclosure include, but are not limited to, other multipotent or pluripotent cells or stem cells, or bone marrow cells. The cells of different types may be admixed with a composition of the disclosure immediately or shortly prior to administration, or they may be co-cultured together for a period of time prior to administration.

The exact amount of cells to be administered is dependent upon a variety of factors, including the age, weight, and sex of the patient, and the extent and severity of the condition to be treated.

In some instances it may be desirable or appropriate to pharmacologically immunosuppress a subject prior to initiating cell therapy and/or reduce an immune response of a subject against the cellular composition. Means for reducing or eliminating an immune response to the transplanted cells are known in the art. As an alternative, the cells may be genetically modified to reduce their immunogenicity.

In another example, the purified cardiomyocytes may be administered with other beneficial drugs or biological molecules (growth factors, trophic factors). When administered with other agents, they may be administered together in a single pharmaceutical compositions, or in separate pharmaceutical compositions, simultaneously or sequentially with other agents (either before or after administration of the other agents).

The present invention also provides medical devices for use or when used in a method as described herein according to any example. For example, the present disclosure provides a syringe or catheter or other suitable delivery device comprising purified cardiomyocytes or a composition according to the present disclosure. Optionally, the syringe or catheter is packaged with instructions for use in a method as described herein according to any example.

Whilst there has been described in the foregoing description preferred embodiments of the present invention, it will be understood by those skilled in the technology concerned that many variations or modifications in details of design or construction may be made without departing from the present invention.

REFERENCES

1 Burridge, P. W., Keller, G., Gold, J. D. & Wu, J. C. Production of de novo cardiomyocytes: human pluripotent stem cell differentiation and direct reprogramming. *Cell stem cell* 10, 16-28, doi:10.1016/j.stem.2011.12.013 (2012).
2 Laflamme, M. A. & Murry, C. E. Regenerating the heart. *Nature biotechnology* 23, 845-856, doi:10.1038/nbt1117 (2005).
3 Lian, X. et al. Robust cardiomyocyte differentiation from human pluripotent stem cells via temporal modulation of canonical Wnt signaling. *Proceedings of the National Academy of Sciences of the United States of America* 109, E1848-1857, doi:10.1073/pnas.1200250109 (2012).
4 Lian, X. et al. Directed cardiomyocyte differentiation from human pluripotent stem cells by modulating Wnt/β-catenin signaling under fully defined conditions. *Nature protocols* 8, 162-175, doi:10.1038/nprot.2012.150 (2013).
5 Hrvatin, S., Deng, F., O'Donnell, C. W., Gifford, D. K. & Melton, D. A. MARIS: method for analyzing RNA following intracellular sorting. *PloS one* 9, e89459, doi: 10.1371/journal.pone.0089459 (2014).

The invention claimed is:

1. A method of distinguishing and isolating a cardiomyocyte sub-type population from a heterogeneous population of cardiomyocytes in a sample that were differentiated from human pluripotent stem cells, the method comprising:

a. contacting the sample with a Signal Regulatory Protein Alpha (SIRPA) antibody; and isolating the cardiomyocytes bound to the SIRPA antibody to provide a population of cardiomyocytes;

b. contacting the population of cardiomyocytes isolated in (a) with:

i. an antibody or a fragment thereof that binds to cell surface marker JAK2 and an antibody or a fragment thereof that binds to cell surface marker CD200 to provide a sub-type population of ventricular cardiomyocytes, and isolating the cells bound to the antibodies or fragments thereof to provide the sub-type population of ventricular cardiomyocytes;

ii. an antibody or a fragment thereof that binds to Cholinergic Receptor Nicotinic Delta Subunit (CHRND) to provide a sub-type population of atrial cardiomyocytes, and isolating the cells bound to the antibody or a fragment thereof to provide the sub-type population of atrial cardiomyocytes; or iii. an antibody or a fragment thereof that binds to cell surface marker JAK2 and an antibody or a fragment thereof that binds to cell surface marker CD200 to provide a sub-type population of ventricular cardiomyocytes, and an antibody or a fragment thereof that binds to Cholinergic Receptor Nicotinic Delta Subunit (CHRND) to provide a sub-type population of atrial cardiomyocytes, and isolating the cells bound to the antibodies or fragments thereof to provide the sub-type populations of ventricular cardiomyocytes and atrial cardiomyocytes.

2. The method according to claim 1, wherein the method further comprises, prior to contacting, generating a culture of the human pluripotent stem cells and causing differentiation of the human pluripotent stem cells into the heterogeneous population of cardiomyocytes in the sample.

3. The method according to claim 1, wherein the antibody is labelled with a detectable moiety.

4. The method according to claim 3, wherein the detectable moiety is selected from the group consisting of: a fluorescent moiety, a luminescent moiety, a chemiluminescent moiety, a radioactive moiety, an enzymatic moiety and a secondary antibody.

5. The method according to claim 1, wherein the isolated cardiomyocyte sub-type population of (b) comprises a population of cells having at least 85% purity.

6. The method according to claim 1, wherein the cardiomyocyte populations are isolated using fluorescent activated cell sorting.

7. The method according to claim 1, wherein the human pluripotent stem cells are ES03 cells, BJ induced pluripotent stem cells (iPS) cells, or both ES03 and BJ iPS cells.

8. A method for detecting cardiomyocytes in a sample comprising a heterogeneous population of cardiomyocytes, the method comprising:

a. contacting the sample with a Signal Regulatory Protein Alpha (SIRPA) antibody; and isolating the cardiomyocytes bound to the SIRPA antibody to provide a population of cardiomyocytes;

b. contacting the population of cardiomyocytes isolated in (a) with:

i. an antibody or a fragment thereof that binds to cell surface marker JAK2 and an antibody or a fragment thereof that binds to cell surface marker CD200 to provide a sub-type population of ventricular cardiomyocytes, and isolating the cells bound to the antibodies or fragments thereof to provide the sub-type population of ventricular cardiomyocytes;

ii. an antibody or a fragment thereof that binds to Cholinergic Receptor Nicotinic Delta Subunit (CHRND) to provide a sub-type population of atrial cardiomyocytes, and isolating the cells bound to the antibody or a fragment thereof to provide the sub-type population of atrial cardiomyocytes; or iii. an antibody or a fragment thereof that binds to cell surface marker JAK2 and an antibody or a fragment thereof that binds to cell surface marker CD200 to provide a sub-type population of ventricular cardiomyocytes, and an antibody or a fragment thereof that binds to Cholinergic Receptor Nicotinic Delta Subunit (CHRND) to provide a sub-type population of atrial cardiomyocytes, and isolating the cells bound to the antibodies or fragments thereof to provide the sub-type populations of ventricular cardiomyocytes and atrial cardiomyocytes.

9. The method according to claim 8, wherein the cardiomyocytes are detected by immunohistochemistry.

10. The method according to claim 8, wherein the sample is a mixed population of cells comprising cardiomyocytes.

* * * * *